United States Patent [19]

Lewis et al.

[11] Patent Number: 5,093,317

[45] Date of Patent: Mar. 3, 1992

[54] TREATING DISORDERS BY APPLICATION OF INSULIN-LIKE GROWTH FACTOR

[75] Inventors: Michael E. Lewis, Landenberg; James C. Kauer, Kennett Square; Kevin R. Smith, Downington, all of Pa.; Kathleen V. Callison, Merchantville, N.J.; Frank Baldino, Jr., Landenberg, Pa.

[73] Assignee: Cephalon, Inc., West Chester, Pa.

[21] Appl. No.: 361,595

[22] Filed: Jun. 5, 1989

[51] Int. Cl.$^5$ .................. A61K 37/36; A61K 37/26
[52] U.S. Cl. ........................................ 514/12; 514/3; 514/4; 514/885; 514/903; 514/21; 424/556; 424/570
[58] Field of Search ............... 424/98, 556, 570; 514/3, 4, 12, 21, 885, 903

[56] References Cited

U.S. PATENT DOCUMENTS

| | | | |
|---|---|---|---|
| 4,341,762 | 7/1982 | Haast . | |
| 4,511,390 | 4/1985 | Kauer | 71/88 |
| 4,699,875 | 10/1987 | Appel | 435/4 |
| 4,783,524 | 11/1988 | Larsen et al. | 530/350 |
| 4,801,575 | 1/1989 | Pardridge | 514/4 |

FOREIGN PATENT DOCUMENTS

| | | |
|---|---|---|
| 88303855.6 | 4/1988 | European Pat. Off. . |
| 59-065058 | 4/1984 | Japan . |
| 63-196524 | 8/1988 | Japan . |
| 8801393 | 4/1988 | PCT Int'l Appl. . |
| 8802760 | 8/1988 | PCT Int'l Appl. . |
| 90/03166 | 6/1990 | PCT Int'l Appl. . |
| 8801693 | 5/1988 | World Int. Prop. O. . |
| 89/01343 | 2/1989 | World Int. Prop. O. . |

OTHER PUBLICATIONS

Baxter et al., Comp. Biochem. Physiol. 91B:229–235 (1988).
Daughaday et al., Endocrine Rev. 10:68–91 (1989).
D'Ercole, J. Devel. Physiol. 9:481–495 (1987).
Hintz et al., Horm. Metab. Res. 20:344–347 (1988).
Baskin et al., TINS 11:107–111 (1988).
Sara et al., Proc. Natl. Acad. Sci. USA 83:4904–4907 (1986).
Francis et al., Biochem. J. 251:95–103 (1988).
Sara et al., Neurosci. Let. 34:39–44 (1982).
Aizenman et al., Brain Res. 406:32–42 (1987).
Fellows et al., Soc. Neurosci. Abstr. 13:1615 (1987).
Onifer et al., Soc. Neurosci. Abstr. 13:1615 (1987).
Bothwell, J. Neurosci. Res. 8:225–231 (1982).
Recio-Pinto et al., J. Neurosci. 6:1211–1219 (1986).
Recio-Pinto and Ishii, J. Neurosci. Res. 19:312–320 (1988).
Mattson et al., J. Cell Biol. 102:1949–54 (1986).
Sara et al., J. Dev. Physiol. 1:343–350 (1979).
Sara et al., Prog. Brain Res. 73:87–99 (1988).
Sara et al., Neurobiol. Aging 3:117–120 (1982).
Nilsson et al., Neurosci. Let. 88:221–226 (1988).
Hansson et al., Acta Physiol. Scand. 132:35–41 (1988).
Sjoberg et al., Brain Res. 485:102–108 (1989).
Coy et al., Biochem. Biophys. Res. Commun. 73:632–8 (1976).
Pardridge, Endocrine Reviews 7:314–330 (1986).
Blundell et al., Fed. Proc. 42:2592–2597 (1983).
Kastin et al., Pharmac. Biochem. Behav. 11:713–716 (1979).
Rapoport et al., Science 207:84–86 (1980).
Pardridge et al., Biochem. Biophys. Res. Commun. 146:307–313 (1987).

(List continued on next page.)

Primary Examiner—F. T. Moezie
Attorney, Agent, or Firm—Fish & Richardson

[57] ABSTRACT

Method of enhancing the survival of neuronal cells, more preferably non-mitotic neuronal cells and/or cholinergic cells in a mammal, which cells are at risk of dying, which method includes administering to the mammal an effective amount of a functional derivative of Insulin-like Growth Factor I or Insulin-like Growth Factor II.

4 Claims, 3 Drawing Sheets

OTHER PUBLICATIONS

Riekkinen et al., Peptides 8:261–265 (1987).
Creveling et al., Experientia 25:26–27 (1969).
Bodor et al., Science 214:1370–1372 (1981).
Smith et al., Pharm Res. (in press).
McManaman et al., Dev. Biol. 112:248–252 (1985).
Schwartz et al., Dev. Brain Res. 1:403–413 (1981).
Kanje et al., Brain Res. 381:24–28 (1986).
Hansson et al. Act & Physiol. Scand. 126:609–614 (1986).
Sara et al. Biol. Psychiat. 18:803–811 (1983).
MacDonnell et al., Proc. Natl. Acad. Sci. USA 74:4681–4684 (1977).
Schwartz et al., Archives of Biochemistry & Biophysics 181:542–549 (1977).
Hintz et al., J. Clinical Endocrinology and Metabolism 54:442–446.
Russell et al., Life Sciences 19:1297–1306 (1976).
Rinehart et al., Proc. Natl. Acad. Sci. USA 82:4365–4368 (1985).

FIG. 6

TREATING DISORDERS BY APPLICATION OF INSULIN-LIKE GROWTH FACTOR

BACKGROUND OF THE INVENTION

The present invention relates to therapeutic polypeptides useful, e.g., for the treatment of neurological and other disorders.

Insulin-like growth factors (IGFs) have been identified in various animal species as polypeptides that act to stimulate growth of cells in a variety of tissues (see Baxter et al., Comp. Biochem. Physiol. 91B:229-235 (1988); and Daughaday et al., Endocrine Rev. 10:68-91 (1989) for reviews), particularly during development (see D'Ercole, J. Devel. Physiol. 9:481-495 (1987) for review). The IGFs, each of which has a molecular weight of about 7,500 daltons, are chemically related to human proinsulin: i.e. they possess A and B domains that (1) are highly homologous to the corresponding domains of proinsulin, and (2) are connected by a smaller and unrelated C domain. A carboxyl-terminal extension, the D domain, is also present in IGFs but is not found in proinsulin.

Certain polypeptide fragments of the IGFs have proven to be useful as antigens to raise antibodies specific for each of the IGFs (see, e.g., Japanese Patent Application No. 59065058; Hintz and Liu, J. Clin. Endocr. Metab. 54:442-446 (1982); Hintz et al., Horm. Metab. Res. 20:344-347 (1988)). Using labelled IGF-specific antibodies as a probe, IGF-I and IGF-II (sometimes respectively termed "somatomedin C" and "somatomedin A") have been found in a variety of tissues, including the mammalian central nervous system (CNS); the presence in the CNS of mRNAs encoding these polypeptides suggests local synthesis in the CNS (see Baskin et al., TINS 11:107-111 (1988) for review). In addition, IGF-III (or "brain IGF"), a truncated form of IGF-I lacking the latter protein's three N-terminal amino acid residues, has been found in fetal and adult human brain (Sara et al., Proc. Natl. Acad. Sci. USA 83:4904-4907 (1986), as well as in colostrum (Francis et al., Biochem. J. 251:95-103 (1988)). Two different IGF receptors have been identified in the adult human CNS (Baskin et al., 1988), including in the brain (Sara et al., Neurosci. Let. 34:39-44 (1982)). In addition, European Patent Application No. 86850417.6 describes evidence for a third type of IGF receptor located in human fetal membranes. Complicating research in this area are (1) evidence that the insulin receptor of brain membranes recognizes not only insulin but also the IGFs; (2) the finding that one of the two types of adult IGF receptors exhibits some affinity for insulin as well as for both IGF-I and II, and (3) current uncertainty as to the physiological significance of binding of IGF-II to the second type of adult IGF receptor (Baskin et al., 1988).

IGF-I and IGF-II appear to exert a stimulatory effect on development or proliferation of a wide range of susceptible cell types (see Daughaday et al., 1989 for review). Treatment with the IGFs or with certain polypeptide fragments thereof has been variously suggested as a bone repair and replacement therapy (European Patent Application No. 88303855.6), as a means to counteract certain harmful side effects of carcinostatic drugs (Japanese Patent Application No. 63196524), and as a way to increase lactation and meat production in cattle and other farm animals (Larsen et al., U.S. Pat. No. 4,783,524). Each of the IGFs also appears to enhance the survival, proliferation and/or neurite outgrowth of cultured embryonic neurons (which, unlike mature neurons, have not yet lost their ability to undergo cell division) from various parts of the CNS (Aizenman et al., Brain Res. 406:32-42 (1987); Fellows et al., Soc. Neurosci. Abstr. 13:1615 (1987); Onifer et al., Soc. Neurosci. Abstr. 13:1615 (1987); European Patent Application No. 86850417.6, and from the peripheral nervous system (Bothwell, J. Neurosci. Res. 8:225-231 (1982); Recio-Pinto et al., J. Neurosci. 6:1211-1219 (1986)). In addition, the IGFs have been shown to affect the development of undifferentiated neural cells: human neuroblastoma tumor cells were shown to respond to added IGFs by extending neurites (Recio-Pinto and Ishii, J. Neurosci. Res. 19:312-320 (1988)) as well as by undergoing mitosis (Mattson et al., J. Cell Biol. 102:1949-54 (1986). As the induction of the enzyme ornithine decarboxylase has been shown to correlate with the stimulation of mitotic activity of these cells, an assay for cell proliferation has been developed based upon measuring the level of activity of this enzyme (Mattsson et al., 1986).

In vivo studies also support the hypothesis that the IGFs play a role in development and differentiation of the immature peripheral and central nervous systems (Sara et al., J. Dev. Physiol. 1:343-350 (1979); Philipps et al., Pediatr. Res. 23:298-305 (1988); Sara et al., Prog. Brain Res. 73:87-99 (1988)), although the physiological nature of this role remains uncertain. Once the neuronal cells of the CNS reach maturity, they do not undergo further cell division.

Neurotrophic factors other than the IGFs have been proposed as a potential means of enhancing neuronal survival, for example as a treatment for the neurodegenerative diseases amyotrophic lateral sclerosis (using skeletal muscle-derived proteins having apparent molecular weights in the 20,000-22,000 dalton and 16,000-18,000 dalton ranges: PCT Application No. PCT/US88/01393), and Alzheimer's disease (using phosphoethanolamine: PCT Application No. PCT/US88/01693). Sara et al., although finding a "significant elevation" in serum and cerebrospinal fluid somatomedin (IGF) levels in patients suffering from Alzheimer's disease compared to normal controls, nevertheless conclude:

Whether somatomedins play a casual (sic) role in the etiology of the dementia disorders of the Alzheimer type remains to be determined. However, since somatomedins stimulate the uptake of amino acids into brain tissue, their administration may provide beneficial therapeutic effects. Finally, the fall in somatomedins observed in normal elderly patients raises the general question of their role in cell aging. (citation omitted; Sara et al., Neurobiol. Aging 3:117-120, 119 (1982)).

In a report that IGF-I, but not IGF-II, stimulates the immediate (i.e. within 20 min.) release of acetylcholine from slices of adult rat brain, a process thought to be related to transitorily increased neurotransmission of acetylcholine rather than to increased cholinergic enzyme activity, Nilsson et al., Neurosci. Let. 88:221-226, 221, 224 (1988), point out that

[One] of the major deficits in Alzheimer's disease concerns the cholinergic system of the brain, where a reduced synthesis and release of [acetylcholine] has been found.... It is of considerable importance to further investigate the role of IGFs in neurodegenerative disorders such as Alzheimer's disease ... (citations omitted).

Using antibody specific for IGF-I to detect an increase in the presence of IGF-I in injured peripheral nerves, notably in the non-neuronal cells named "Schwann cells", Hansson et al., Acta Physiol. Scand. 132:35-41, 38, 40 (1988), suggest that Thus, increased IGF-I immunoreactivity is observed in regenerating peripheral nerves after any injury and seems to form part of a general reaction pattern, most evident in the Schwann cells. Our ultrastructural studies have revealed that the Schwann cells undergo hypertrophy after vibration trauma, and show signs of activation, i.e. the granular endoplasmic reticulum and Golgi complex increased in extent. We thus interpret the increase in IGF-I immunoreactivity in the Schwann cells, documented in this study on vibration-exposed nerves, as part of a transient, reactive response beneficial for the early stages of repair processes.... We consider the increase in IGF-I immunoreactivity to reflect mainly the initial reactions in a chain of events resulting in repair of the injured tissue or organ [although this increase] may be interpreted to reflect disturbed axoplasmic transport [of IGF-I molecules], due in part to the diminution of microtubules reported to occur after vibration exposure. (citation omitted)

Further, Sjoberg et al., Brain Res. 485:102-108 (1989), have found that local administration of IGF-I to an injured peripheral nerve stimulates regeneration of the nerve as well as proliferation of associated non-neuronal cells.

Several methods have been employed to decrease the susceptibility of polypeptides to degradation by peptidases, including, e.g., substitution of D-isomers for the naturally-occurring L-amino acid residues in the polypeptide (Coy et al., Biochem. Biophys. Res. Commun. 73:632-8 (1976)). Where the polypeptide is intended for use as a therapeutic for disorders of the CNS, an additional problem must be addressed: overcoming the so-called "blood-brain barrier," the brain capillary wall structure that effectively screens out all but selected categories of molecules present in the blood, preventing their passage into the brain. While the blood-brain barrier may be effectively bypassed by direct infusion of the polypeptide into the brain, the search for a more practical method has focused on enhancing transport of the polypeptide of interest across the blood-brain barrier, such as by making the polypeptide more lipophilic, by conjugating the polypeptide of interest to a molecule which is naturally transported across the barrier, or by reducing the overall length of the polypeptide chain (Pardridge, Endocrine Reviews 7:314-330 (1986); U.S. Pat. No. 4,801,575.

SUMMARY OF THE INVENTION

In general, the invention features a method of enhancing the survival of cells at risk of death, preferably neuronal cells, more preferably non-mitotic neuronal cells and/or cholinergic neuronal cells, in a mammal, preferably in the context of a therapeutic treatment of neuronal tissues which are suffering from the effects of aging, of injury, or of a disease such as Alzheimer's disease, stroke, epilepsy, amyotrophic lateral sclerosis, or Parkinson's disease, by administering to the mammal an effective amount of a functional derivative, e.g., a fragment or analog of IGF-I or of IGF-II, alone or in a biologically active combination with another such functional derivative.

The invention also features a method of enhancing the cholinergic activity (i.e., acetylcholine-synthesizing capacity) of cholinergic neuronal cells in a mammmal, preferably non-mitotic neuronal cells, and preferably in the context of a therapeutic treatment of neuronal tissues which are suffering from the effects of aging, of injury, or of a disease such as Alzheimer's disease, stroke, epilepsy, amyotrophic lateral sclerosis, or Parkinson's disease, by administering to the mammal an effective amount of a functional derivative of IGF-I or of IGF-II, preferably a fragment of IGF-I or IGF-II or, alternatively, an analog of IGF-I, of IGF-II, or of a fragment of IGF-I or IGF-II, alone or in a biologically active combination with another such functional derivative.

The invention also features a method of modifying a ligand, preferably a neuroactive peptide, capable of binding to a receptor located on a cell surface, by first binding the ligand to a preparation of said receptor, then performing the modification procedure/preferably cationization, glycosylation, or increasing the lipophilicity of the polypeptide), and then releasing the modified ligand from the receptor.

The method of the invention uses functional derivatives of IGF-I and of IGF-II to enhance the survival rate and/or the cholinergic activity of mammalian cells at increased risk of death due to some factor such as disease, injury, or natural aging processes, or where stimulation of cholinergic activity could have a beneficial effect on the mammal's condition. Some of the functional derivatives utilized by the method of the invention are known; others may be discovered by applying the routine methods disclosed herein.

Survival of a treated neuronal cell denotes maintenance of the cell's viability to an extent greater than that of untreated control cells. Since the preponderance of neuronal cells of the mature CNS are commonly believed to be incapable of cell division, the ability of an agent to promote the survival of such cells may be measured by an assay indicative of cellular trophic response, such as the ornithine decarboxylase assay disclosed herein. Alternatively, one can utilize any other assay which reproducibly indicates relative numbers of surviving cells, such as directly counting cells which stain as viable cells, or assaying incorporation of appropriate labelled precursors into mRNA or protein. Where the effect of an added IGF or its functional derivative on the functioning of cholinergic neurons is of particular interest, an alternative assay which measures that functioning, such as the choline acetyltransferase assay disclosed herein, may be utilized.

Either approach may be adapted to test the effect of treatment with IGF functional derivatives on particular subsets of neurons known to be vulnerable in specific degenerative diseases, such as spinal cord cholinergic neurons in amyotrophic lateral sclerosis. A preliminary screen for polypeptides which bind to the IGF receptors may first be employed to indicate likely candidates for the cell survival or cholinergic activity assay; disclosed herein is an IGF-I-receptor displacement assay designed for such a purpose. Those polypeptides which appear to promote cell survival or cholinergic activity under one or more of the above assays may be further tested, by appropriate in vivo administration, for their ability to counteract the degenerative effects of aging, injury or disease in the nervous system or other tissue of an animal.

The use of any polypeptide as a therapeutic raises the issue of stability of the polypeptide after administration to the organism, when it is exposed to the action of various peptidases both within and without the target tissue. Where lack of such stability is expected to be a problem, certain stability-enhancing modifications disclosed herein may be made to the polypeptide. Other modifications designed to facilitate transport of the polypeptide across the blood-brain barrier may be made to the polypeptide, as disclosed herein.

The method of the invention is useful for therapeutically treating a disorder of a human or other mammal characterized by the death of cells, particularly neural cells, including disorders attributable to a disease or aging of, or injury to, such neuronal cells. The neurotrophic peptides, including the IGFs and/or their functional derivatives, are useful for the treatment of neurodegenerative diseases such as Alzheimer's disease, stroke, epilepsy, amyotrophic lateral sclerosis and Parkinson's disease, as well as general age-related neuronal loss, conditions which have proven particularly intractible to treatment by alternative methods.

Other features and advantages of the invention will be apparent from the following description of the preferred embodiments thereof, and from the claims.

DESCRIPTION OF THE PREFERRED EMBODIMENTS

The drawings are first described.

DRAWINGS

THE PEPTIDES

The present invention is directed to the modification of neuroactive polypeptides such as IGF-I and IGF-II and their functional derivatives, and their use as therapeutics for certain neurological diseases or disturbances characterized by increased vulnerability of neurons to dying. A "neuroactive polypeptide" is defined as a polypeptide which exerts a cell surface-receptor mediated effect on neuronal cells: e.g., the IGFs, Nerve Growth Factor (NGF), Epidermal Growth Factor, Fibroblast Growth Factor, and insulin. A "functional derivative" of a polypeptide is a compound which is a fragment or an analog of that molecule and which possesses the desired biological activity, herein defined as the ability to promote survival and/or cholinergic activity of neuronal cells. A "fragment" of a polypeptide refers to any polypeptide subset of that polypeptide. An "analog" of a polypeptide refers to a molecule having biological activity but possessing some structural differences compared to the polypeptide: e.g., an altered amino acid sequence, or the presence of additional chemical moieties not normally a part of the molecule. Such moieties (introduced, for example, by acylation, alkylation, cationization, or glycosylation reactions) may improve the molecule's solubility, absorption, transport, biological halflife, etc. Alternatively, or in addition, some moieties may decrease the toxicity of the molecule, or eliminate or attenuate any undesirable side effect of the molecule. Moieties capable of mediating such effects are disclosed in *Remington's Pharmaceutical Sciences* (Mack Pub. Co., Easton, Pa., 1980). Although some derivatives of IGF-I or IGF-II may be inoperative, a person skilled in the art disclosed herein can recognize which are operative and which are not, as will be explained in more detail below.

Some of the compounds within the scope of this invention are depicted in Table 1, which shows the amino acid sequences (expressed using single-letter abbreviations as defined in Table 2) of IGF-I, IGF-II, and a number of functional derivatives of IGF-I and IGF-II. These derivatives were selected for study on the basis of one or more of the following criteria, which are related to the ability to bind to IGF-I or IGF-II receptors, and thus are useful for identifying additional functional derivatives of the invention: (1) conservation of amino acid sequence among species; (2) presence of "conservative" amino acid substitutions among species (i.e., amino acids with similar shape, charge or other salient characteristics); (3) receptor shielding of tyrosine residues from radioiodination (Maly and Luthi, J. Biol. Chem. 263:7068-7072 (1988); (4) predominance of hydrophilic residues, suggesting the location of a receptor-binding domain on the surface of the polypeptide, a presumptive requirement for receptor interaction; and (5) consideration of hydrophobic and polar regions of three-dimensional models (e.g., Blundell et al., Fed. Proc. 42:2592-2597 (1983) and identifying therefrom regions which are possible binding sites.

Since the ability of peptides to penetrate the blood-brain barrier is related to their lipophilicity or their net ionic charge, suitable modifications of these peptides (e.g., by substituting pentafluorophenylalanine for phenylalanine, or by conjugation to cationized albumin) to increase their transportability (Kastin et al, Pharmac. Biochem. Behav. 11:713-716 (1979); Rapoport et al., Science 207:84-86 (1980); Pardridge et al., Biochem. Biophys. Res. Commun. 146:307-313 (1987); Riekkinen et al., Peptides 8:261-265 (1987)) may be important for their bioavailability following administration outside the blood-brain barrier, and these modifications are within the scope of the invention. In addition, since bioavailability of peptides may be limited by their susceptibility to degradation by proteases and peptidases (Littlewood et al., Neurochem. Int. 12:383-389 (1988)), modifications of these peptides (e.g., replacement of L-amino acids with D-amino acids) to increase their metabolic stability (Coy et al., 1976) may also be important for their therapeutic efficacy, and these modified peptides are also within the scope of the invention.

Functional derivatives of the invention include, among others, peptides which vary from the native IGF molecules in any one or more of the following ways:

1. Chemical modification of the amino and carboxyl groups present at the respective ends of the peptides.
2. Replacement of one or more of the amino acid residues in the native sequence with biologically compatible other amino acid residues.
3. Replacement of one or more of the amino acid residues in the native sequence with chemically modified, biologically compatible other amino acid residues.
4. Deletion of one or more of the amino acid residues in the native sequence.
5. Repetition of one or preferably a sequence of several amino acid residues in the native sequence, with or without chemical modification to, or replacement or deletion of, one or more of the members of the sequence.
6. Cyclization, that is, joining the amino and carboxyl ends of the linear peptide.
7. Linkage of a fragment of IGF-I or II with another molecule such as a polypeptide (e.g., another fragment of IGF-I or II) or a carbohydrate, by means of a disulfide, peptide, ester or other covalent bond.

The invention also utilizes as a preferred subgroup within the functional derivatives described above, those functional derivatives having the sequence: $R_1$-$AA_1$-$AA_2$-$AA_3$-$AA_4$ ... $AA_n$-$R_2$, wherein $AA_1$, $AA_2$, $AA_3$, $AA_4$ ... $AA_n$ are amino acid residues of the IGF-peptide subsets or are conservative replacements for them as defined in Table 2, and n is any integer from 5 to 70 for IGF-I functional derivatives and 5-67 for IGF-II functional derivatives. $R_1$ is attached to the amino group $AA_1$ and selected from the group of hydrogen, lower ($C_{1-6}$) alkyl, lower alkyl carbonyl, lower alkenyl, lower alkynyl, formyl, lower ($C_{6-10}$) aryl, aroyl, aryloxy-carbonyl, aralkyloxy-carbonyl, lower alkyloxycarbonyl, benzoyl, 1- or 2-thenoyl, nicotinoyl, dihydronicotinoyl, N-alkyldihydronicotinoyl, isonicotinoyl, and N-alkyldihydroisonicotinoyl. The carboxyl-terminal substituent ($R_2$) of the peptides is selected from the following: OH; $NH_2$; $OR_3$, wherein $R_3$ is a lower alkyl or a lower aryl; $OR_3OH$, wherein $R_3$ is defined as above; and $NH$-$R_3$ or $N(CH_3)R_3$, wherein $R_3$ is defined as above. Alternatively, the carboxyl group of the carboxyl-terminal amino acid may be replaced by any one of $-PO_3H_2$, $-B(OH)_2$, $-CH_2OH$, $-SO_3H$ or a 5-tetrazole group.

The amino-terminal amino group and/or the lysine, serine or threonine side chains occurring within the peptide may optionally be acylated by formyl, acetyl, propionyl, and similar lower alkylacyl residues or by aryl or heterocyclic acyl residues such as benzoyl, thenoyl, nicotinoyl, isonicotinoyl, n-alkylnicotinoyl and their dihydro and tetrahydro derivatives. Such modifications would be expected to enhance the blood-brain barrier permeability of the therapeutic agent (Creveling et al., Experientia 25:26-27 (1969); Bodor et al., Science 214:1370-1372 (1981)).

In peptide sequences containing proline, glutamic acid, or aspartic acid at the amino-terminus, the amino terminal amino acid may optionally be replaced by L-pyroglutamic acid.

The fragment polypeptides of IGF-I and IGF-II are subsets of the corresponding IGF molecules containing fewer amino acid residues than the native molecules. Preferred are sequences of 5-40 residues and most preferred are sequences of 6-25 residues. A portion of the amino acids of these sequences may be substituted with conservative replacements or deletions which improve the chemical or biological stability of the product peptides or improve their transport across the blood-brain barrier. Preferably, no more than 30% and more preferably no more than 20%, of the amino acid residues are replaced or deleted. A listing of suitable conservative replacements is given in Table 2, along with a key to the single-letter abbreviations for the common, naturally-occurring amino acid residues found in proteins. Certain other abbreviations used in Table 2 are herein defined: by Nle is meant norleucine, by Aib is meant aminoisobutyric acid, by AdaA is meant $\beta$-adamantylalanine, by AdaG is meant $\alpha$-adamantylglycine, by homo-Arg is meant L-homoarginine, by D-homo-Arg is meant D-homoarginine, by Acp is meant $\epsilon$-aminocaproic acid, by Chg is meant L-$\alpha$-cyclohexylglycine, and by allo-Thr is meant L-allothreonine. Additionally, by Cha is meant $\beta$-cyclohexyl-alanine, by Me is meant methyl ($CH_3$), by Orn is meant ornithine, by pyro-Glu is meant the pyroglutamyl group, by Met(O) and D-Met(O) are meant the sulfoxides derived from L- and D-methionine, respectively, by $\beta$-Ala is meant $\beta$-alanine, by Acm is meant acetamidomethyl, by L-Dopa is meant 3-(3,4-dihydroxyphenyl)-L-alanine, and by Bpa is meant 4-benzoyl-phenylalanine.

The symbolism and abbreviations used are otherwise those recommended by the IUPAC-IUB Joint Commission on Biochemical Nomenclature, "Nomenclature and Symbolism for Amino Acids and Peptides, Recommendations 1983" J. Biol. Chem. 260:14-42 (1985). As is conventional, these same symbols are used to define the corresponding residues of the amino acids when they are linked into a peptide chain. Where the amino acid residue has isomeric forms, it is the L-form of the amino acid that is represented unless otherwise expressly indicated. In accordance with conventional representation, the amino group at the N-terminus of each peptide appears to the left and the carboxyl group at the C-terminus to the right.

Besides the amino acid substitutions suggested above, other methods of improving transport of the polypeptide across the blood-brain barrier, such as chemical modification of the polypeptide, may be employed. In any chemical modification procedure, the polypeptide may first be attached to its receptor in order to protect and maintain the receptor-binding site structure during the chemical modification process, which can comprise, for example, cationization (according to the method, for example, of Pardridge et al., 1987) or glycosylation (according to the method of Schwartz et al., Arch. Biochem. Biophys. 181:542-549 (1977)).

USES OF THE PEPTIDES

As described more fully below, the present invention provides a novel use of IGF-I and IGF-II and their functional derivatives, as agents for the treatment of diseases or disturbances characterized by an increased risk of cell death, including in particular, neuronal cell death. The bioactivity of each polypeptide of the invention may be conveniently assayed by either a brain ornithine decarboxylase assay or a spinal cord choline acetyl transferase assay, both of which are described in detail below. Alternatively, the polypeptides may first be screened by the receptor-IGF-I displacement assay described below, which measures the polypeptide's ability to displace labelled IGF-I bound to receptors in homogenized brain tissue. This assay has been demonstrated to correlate with the polypeptide's bioactivity as measured by the two enzymatic assays. As described in the examples below, these assays disclose previously unknown bioactivity of IGF-I, IGF-II, IGF-III and some functional derivatives of these molecules. Thus, the peptides of this invention should be useful for administration to humans or other mammals who suffer from neurological diseases or disturbances characterized by increased risk of neuronal cell death, as described above. These neurological diseases or disturbances include but are not limited to: Alzheimer's disease, Parkinson's disease, amyotrophic lateral sclerosis, stroke, and concussive or penetrating injuries of the brain or spinal cord.

The formulations of this invention are useful for parenteral administration, for example, intravenous, subcutaneous, intramuscular, intraorbital, ophthalmic, intraventricular, intracranial, intracapsular, intraspinal, intracisternal, intraperitoneal, topical, intranasal, aerosol, scarification, and also for oral, buccal, rectal or vaginal administration. The compositions can be formulated for parenteral administration to humans or other mammals in therapeutically effective amounts (e.g., amounts which eliminate or reduce the patient's pathological condition) to provide therapy for the neurological diseases described above.

The compounds provided herein can be formulated into pharmaceutical compositions by admixture with pharmaceutically acceptable nontoxic excipients and carriers. As noted above, such compositions may be prepared for use as parenteral administration, particularly in the form of liquid solutions or suspensions; for oral administration, particularly in the form of tablets or capsules; or intranasally, particularly in the form of powders, nasal drops, or aerosols.

The compositions may conveniently be administered in unit dosage form and may be prepared by any of the methods well known in the pharmaceutical art, for example, as described in *Remington's Pharmaceutical Sciences*. Formulations for parenteral administration may contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the peptides. Other potentially useful parenteral delivery systems for these peptides include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration.

The materials of this invention can be employed as the sole active agent in a pharmaceutical or can be used in combination with other active ingredients, e.g., other growth factors which could facilitate neuronal survival in neurological diseases, or peptidase or protease inhibitors.

The concentration of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution containing about 0.1 to 10% w/v compound for parenteral administration. Typical dose ranges are from about 1 $\mu$g/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the neurological disease, the overall health status of the particular patient, the relative biological efficacy of the compound selected, the formulation of the compound excipients, and its route of administration.

The present invention will be further illustrated by the following examples. These examples are not be construed as limiting the scope of the invention, which is to be determined solely by the appended claims.

EXAMPLE 1

Recombinant human IGF-I, IGF-II, and IGF-III, as well as several chemically synthesized peptides consisting of partial sequences of IGF-I or IGF-II, were obtained from commercial sources as indicated in Table 1. $^{125}$I-labeled [Threonine$^{59}$]IGF-I was obtained from Amersham (Arlington Heights, IL). Other peptides consisting of partial sequences of IGF-I or IGF-II were chemically synthesized using Fmoc chemistry on a Milligen Biosearch Model 9600 Peptide Synthesizer, and purified on Hewlett-Packard Models 1050 and 1090M HPLCs according to the method of Hudson, J. Org. Chem. 53:617-624 (1988). Fmoc amino acids, BOP (Castro's reagent), and resins were purchased from Biosearch (San Raphael, CA 94901) and Bachem Bioscience, Inc. (Philadelphia, PA 19104). Solvents were purchased from Burdick and Jackson (Muskegon, MI 49442). Other reagents were purchased from Sigma Chemical Co. (St. Louis, MO 63178).

Brain tissue containing the cerebral cortex and cerebellum was dissected from adult Sprague-Dawley rats (Hilltop Lab Animals, Inc. Scottsdale, PA) and homogenized at low power for 5 minutes in a Brinkmann Polytron homogenizer (Westbury, NY) containing 50 volumes of ice-cold buffer consisting of 10 mM HEPES, 0.5% BSA, 0.0125% NEM, 0.025% bacitracin, and 100 KIU/ml aprotinin, pH 7.6 (Bohannon et al., Endocrinology 119:943-945 (1986). Following homogenization, the tissue was collected after centrifugation at 7800×g for 20 minutes and resuspended in 10 volumes of assay buffer. Tissue (50 $\mu$l), 100 $\mu$l $^{125}$I-[Threonine$^{59}$]IGF-I (20 pM), and 50 $\mu$l of buffer or peptides of varying concentration were added to 96-well plates and incubated on ice for 3 hours. After the incubation period, the tissue was collected on Whatman GF/C filters that had been pre-soaked in 0.01% polyethylenimine and washed four times with ice-cold assay buffer using a Brandel cell harvester (Gaithersburg, MD). The filters were removed and the bound $^{125}$I-[Threonine$^{59}$]IGF-I was measured using a Beckman Model 5500B Gamma Counter.

Table 3 summarizes the results of the $^{125}$I-[Threonine$^{59}$]IGF-I displacement assay utilizing native IGFs and IGF fragments. The results demonstrate that, while IGF-I and IGF-III are potent displacers of $^{125}$I-[Threonine$^{59}$]IGF-I, IGF-II is essentially inactive, indicating that the assay is selective for the identification of IGF-I-like molecules. In this assay, IGF-I(24-41) alone or in combination with IGF-II(54-67) were active in displacing $^{125}$I-[Threonine$^{59}$]IGF-I. IGF-II(54-67) alone, and several other fragments listed in Table 3 were not significantly effective displacers of $^{125}$I-[Threonine$^{59}$]IGF-I.

TABLE 3

| IGF-I RECEPTOR COMPETITION ASSAY SUMMARY | |
|---|---|
| PEPTIDE (CONC.) | PERCENT MAX. BOUND (SD) |
| IGF-I (10 pM) | 100 (1.1) |
| IGF-I (40 nM) | 9.6 (0.7) |
| IGF-II (40 nM) | 92.1 (0.7) |
| IGF-III (40 nM) | 17.6 (2.6) |
| IGF-I(24-41) (100 μM) | 44 (7) |
| IGF-I(24-41) (50 μM) | 99 (6) |
| IGF-I(24-41) (50 μM) + IGF-II(54-67) (50 μM) | 49 (11) |
| IGF-II(54-67) (100 μM) | 94 (6) |
| IGF-I(62-70) (100 μM) | 83 (20) |
| IGF-I(30-41) (100 μM) | 94 (1.4) |
| IGF-II(62-67) (100 μM) | 83 (21) |
| IGF-II(33-40) (1 mM) | 92 (1.8) |

EXAMPLE 2

Brains were removed intact from adult Sprague-Dawley rats, frozen on powdered dry ice, and cut into 20 μm sections (at the level of the cerebellum and brain stem) which were thaw-mounted onto gelatin-coated glass microscope slides (Herkenham and Pert, J. Neurosci. 2:1129-1149 (1982)). Using a modification of the method of Bohannon et al. (1986), the tissue sections were covered with 250 μl of HEPES assay buffer (see Example 1) containing 0.01 nM $^{125}$I-[Threonine$^{59}$]IGF-I alone or in combination with unlabeled IGF-I, IGF-II, or synthetic peptide fragments thereof. The sections were incubated at 4° C. for 24 hours and then rinsed in three 1-minute changes (200 ml each) of ice-cold HEPES assay buffer. The tissue sections were then wiped off the slides with filter paper, and the tissue-bound radioactivity was measured in a Beckman Model 5500B Gamma Counter.

In this assay, in contrast to the assay described in Example 1, $^{125}$I-[Threonine$^{59}$]IGF-I binding was potently displaced by both IGF-I and IGF-II, indicating the utility of this assay for detecting potentially active derivatives of both of these molecules (Table 4). $^{125}$I-[Threonine$^{59}$]IGF-I binding was displaced by IGF-II(3-3-40), but not by IGF-II(54-67).

TABLE 4

| PEPTIDE (CONC.) | PERCENT MAX. BOUND |
|---|---|
| IGF-I (4 pM) | 91 |
| IGF-I (400 pM) | 30 |
| IGF-II (200 nM) | 50 |
| IGF-II (400 nM) | 23 |
| IGF-II (33-40)(1 mM) | 76 |
| IGF-II (33-40)(.10 mM) | 82 |
| IGF-II (54-67)(.25 mM) | 167 |
| IGF-II (54-67)(.025 mM) | 132 |

EXAMPLE 3

The activity of IGF-I, IGF-II, or synthetic peptide derivatives of these molecules was assayed on dissociated cultures of 14-day embryonic rat spinal cord neurons. The spinal cord neurons were obtained from trypsin-dissociated spinal cords, plated, incubated with peptides, and subsequently (48 hr later) assayed for choline acetyltransferase activity as described by McManaman et al., Dev. Biol. 112:248-252 (1985).

Figure 1:
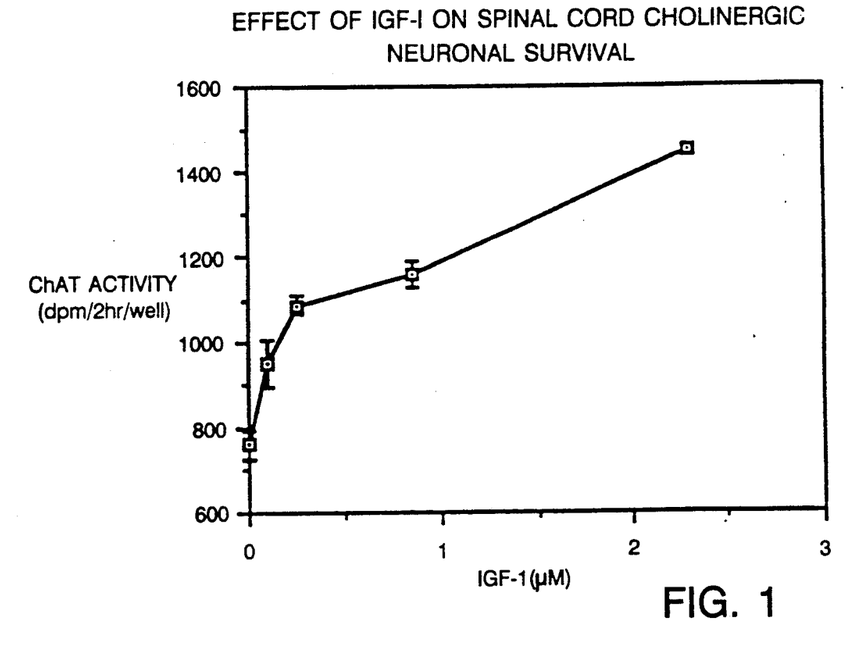
FIG. 1 is a graph illustrating the effect of IGF-I on the survival of cholinergic neurons in rat spinal cord cultures.
Figure 2:
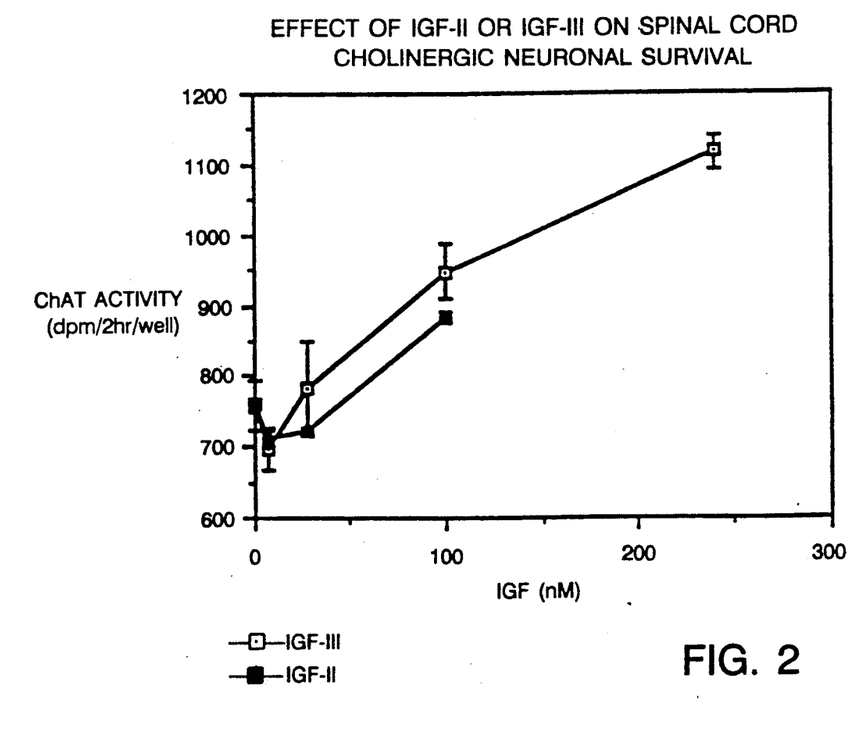
FIG. 2 is a graph showing the effect of IGF-II and IGF-III on the survival of cholinergic neurons in rat spinal cord cultures.
Figure 3:
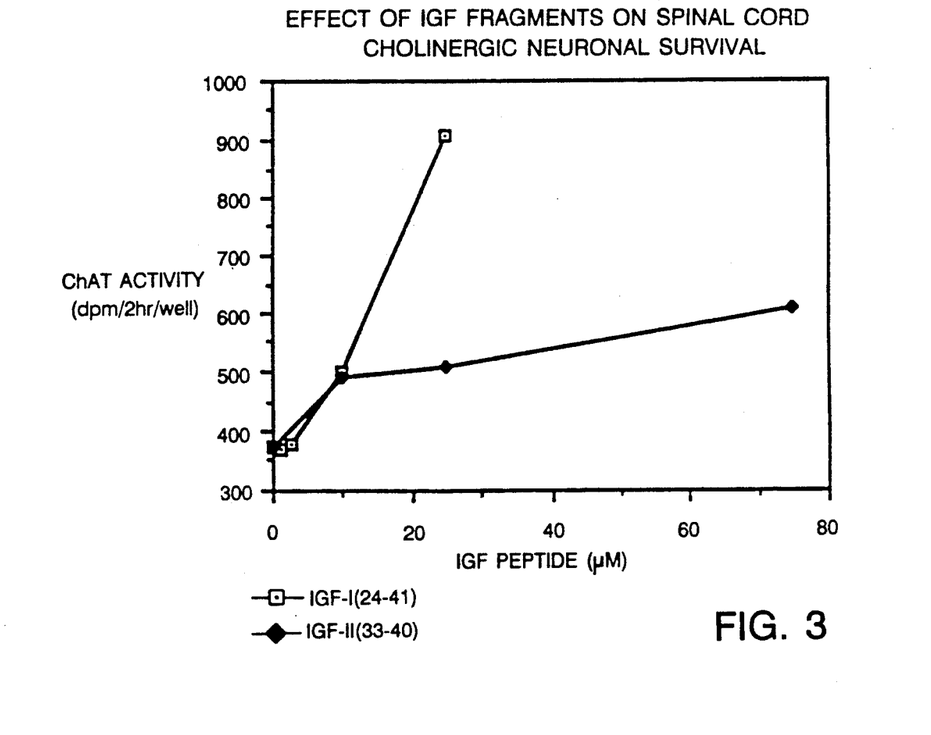
FIG. 3 is a graph illustrating the effect of certain synthetic peptide fragments of IGF-I and IGF-II on the survival of cholinergic neurons in rat spinal cord cultures.

In this assay, IGF-I was found to produce a substantial, dose-dependent increase in choline acetyltransferase activity (FIG. 1), suggesting that IGF-I can dramatically enhance the cholinergic activity of spinal cord cholinergic neurons. Furthermore, IGF-II and IGF-III were found to be active in the spinal cord assay (FIG. 2). In addition, IGF-I(24-41) and IGF-II(33-40) were also found to produce a dose-dependent increase in choline acetyltransferase activity, indicating that each peptide is an active IGF functional derivative (FIG. 3).

EXAMPLE 4

The in vivo activity of IGF-I, IGF-II or synthetic peptide derivatives of these molecules was tested using a biochemical marker for CNS neurotrophic activity, the induction of brain ornithine decarboxylase. The induction (i.e. increased activity) of ornithine decarboxylase has been reported to be a general marker for the actions of a variety of trophic factors. (Schwartz et al., Dev. Brain Res. 1:403-413 (1981); Kanje et al., Brain Res. 381:24-28 (1986); Russell et al., Life Sci. 19:1297-1306 (1976); MacDonnell et al. Proc. Natl. Acad. Sci. USA 74, 4681-4684 (1977); Rinehart et al. Proc. Natl. Acad. Sci. USA 82, 4365-4368 (1985)).

Sprague-Dawley rats, 4 days old, were injected intracerebrally (in the area of the lateral ventricle) with 5 μl of 0.1M phosphate-buffered saline (PBS) containing IGF-I, IGF-II or a synthetic peptide derivative (1.25-2.5 μg dose, with 6 animals per treatment group). After 6 hours, the brains were removed, and ornithine decarboxylase was assayed essentially as described by Lewis et al., Proc. Natl. Acad. Sci. USA 75:1021-1023 (1978).

Figure 4:
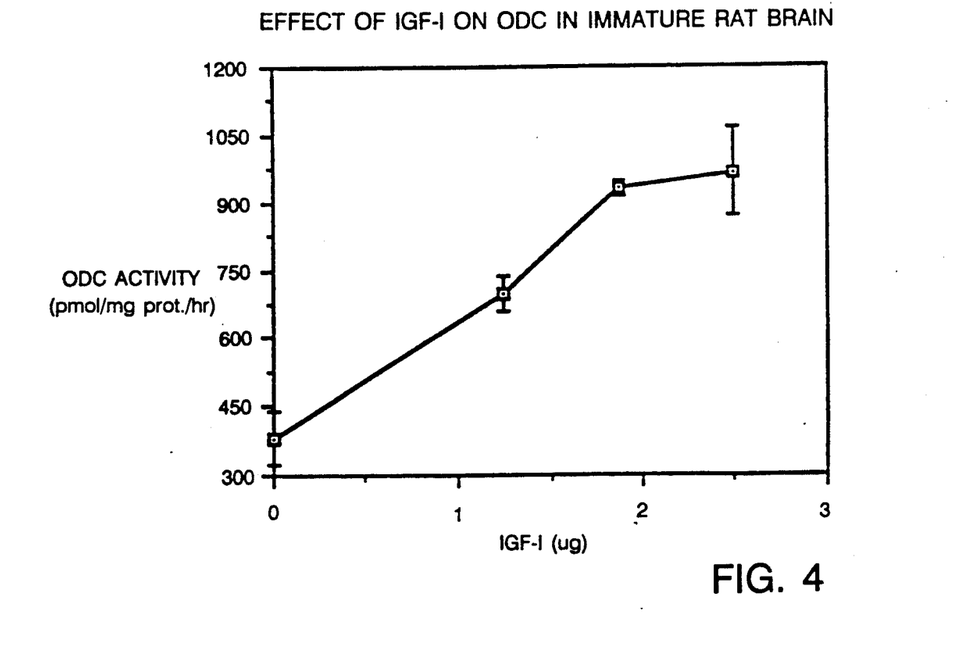
FIG. 4 is a graph depicting the effect on brain ornithine decarboxylase activity of increasing doses of IGF-I injected into the brains of immature rats.
Figure 5:
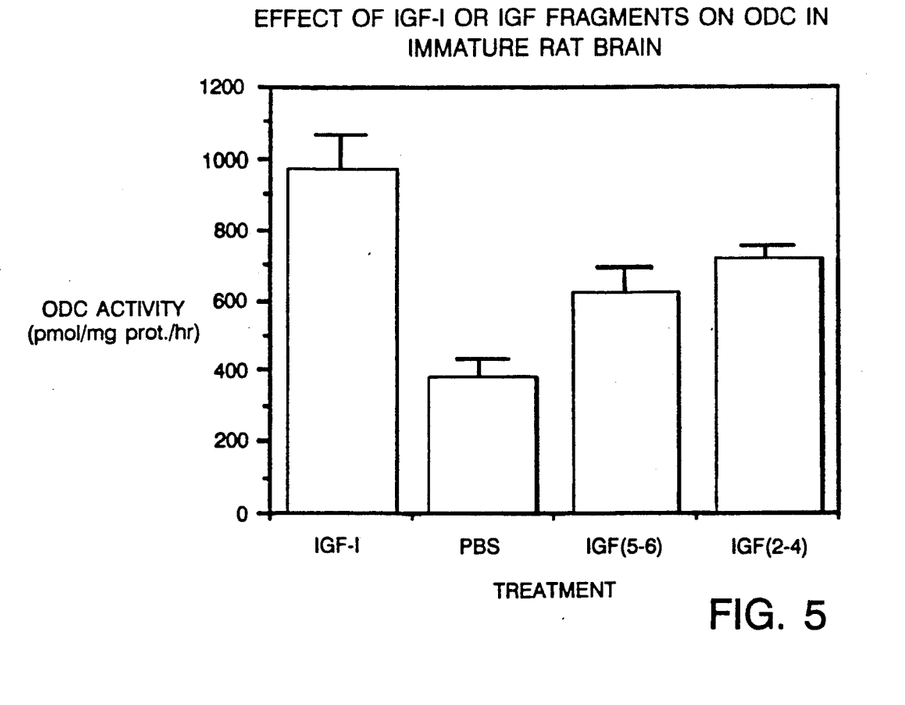
FIG. 5 is a graph showing the effect on brain ornithine decarboxylase activity of injection of IGF-I or synthetic peptide fragments of IGFs into the brains of immature rats.

Administration of IGF-I produced a dose-dependent increase in brain ornithine decarboxylase activity (FIG. 4). In addition, both IGF-I(24-41) and IGF-II(54-67) increased brain ornithine decarboxylase activity (FIG. 5; these peptides are referred to in FIG. 5 as IGF-I (2-4) and IGF-I(5-6), respectively).

EXAMPLE 5

Figure 6:
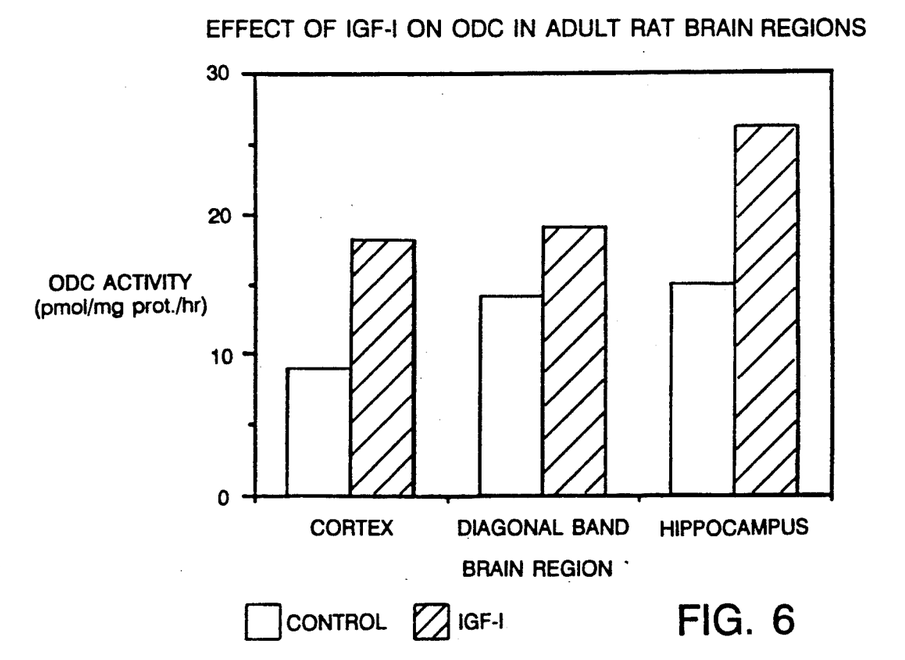
FIG. 6 is a graph depicting the effect on brain ornithine decarboxylase activity of injection of IGF-I into the brains of mature rats.

To determine whether the induction of brain ornithine decarboxylase by IGF-I was limited to developing animals, IGF-I was also injected intraventricularly into the lateral ventricles of adult Sprague-Dawley rats. After 6 hours, the brains were removed, dissected into several regions (cerebral cortex, medial septum, and hippocampus), and then assayed for ornithine decarboxylase activity as described in Example 4. As shown in FIG. 6, IGF-I stimulated ornithine decarboxylase activity in all brain regions assayed. This result indicates that IGF-related molecules have potential utility in widespread regions of the brain.

EXAMPLE 6

Cationization is a process by which free carboxyl groups of acidic amino acid residues on a polypeptide (i.e., aspartic acid and glutamic acid residues) are modified in order to increase the net positive charge on the polypeptide. The process of cationization has been used to enhance the cellular uptake of large molecules such as albumin and horseradish peroxidase into mouse fibroblast cells (Shen et al., Proc. Nat. Acad. Sci. USA 75:1872–1876 (1978)). Kumagai et al., J. Biol. Chem. 262:15214–15219 (1987), using intact microvessels from bovine brain that are reportedly a model system for measuring transport across the blood-brain barrier, showed that uptake of cationized albumin by isolated bovine brain microvessels was enhanced when compared with uptake of native albumin.

For global modification of free carboxyl groups, the polypeptide (e.g., NGF, IGF-I, IGF-II or a functional derivative) would be reacted with excess hexamethylenediamine (HMD) (15.5 g/g total protein) for 30 minutes at room temperature, followed by covalent coupling of HMD with 1-ethyl-3[-3-dimethyl-aminopropyl] carbodiimide hydrochloride (EDAC) (1.0 g/g total protein) for 3 hours at room temperature. Unreacted species may be removed by filtration using Centricon-3 MPS-1 separation devices (Amicon, Danvers, MA) or ion exchange chromatography. The purified polypeptide may be analyzed using isoelectric focusing to determine the amount of cationization.

If the global modification is used on a polypeptide that is a ligand which binds to a cell surface receptor, and the modification produces a molecule lacking biological activity, the cationization process may be repeated as described above except that the polypeptide would be pre-bound to an appropriate receptor prior to cationization, in order to protect the receptor-binding site on the polypeptide. This protection procedure would be carried out as follows: Brain tissue containing receptors for the polypeptide of interest (e.g., IGF-I) is prepared as described above in Example 1. After incubation with the polypeptide ligand for 2 hours at 4° C. to permit receptor binding, the reaction mixture is brought to room temperature, and the cationization procedure carried out using HMD and EDAC as described above. The reaction mixture is then centrifuged at 16,000 rpm at 4° C. for 30 sec in an SS-34 rotor in a Sorvall RC5B centrifuge. The supernatant is discarded and the pellet washed three times in PBS with bovine serum albumin (1 mg/ml). The pellet is resuspended in 100 mM acetic acid and incubated for 10 min @ 4° C. to release the cationized polypeptide from its receptors. After centrifugation again at 16,000 rpm, the supernatant, which contains the released cationized polypeptide, is pH-neutralized with NaOH. It may then be analyzed by isoelectric focusing, by a receptor-binding assay as described in Example 1, or by any appropriate assay for biological activity.

EXAMPLE 7

An alternative to the global modification method is to couple polylysine to at least one free carboxyl group on polypeptide (such as IGF-I, IGF-II, or a functional derivative of either). The procedure follows the method of Shen et al., 1978. For example, polylysine, IGF-I and carbodiimide are added in a 1:1:1 ratio in water or buffer for 3 hours at room temperature. The modified protein would be separated and analyzed as described above in Example 6.

EXAMPLE 8

A third method for modifying protein carboxyl groups to enhance blood brain barrier transport is to form esters with diazomethane or N,N-dimethylformamide R acetals (DMF acetals), where R is dimethyl, diethyl, dibutyl, dibenzyl, etc. This type of modification rapidly forms esters from negatively charged carboxylic acid groups, thus increasing the overall positive charge. An additional benefit from this modification is that these added ester groups may be such that they increase the overall lipophilicity of the polypeptide and may be removed by intrinsic esterases in vivo to yield intact growth factor. The procedure for this modification is to react diazomethane or DMF acetals with the polypeptide in a 1:1 ratio in solution for 30 min. at room temperature, followed by purification and characterization as described above in Example 6.

EXAMPLE 9

A fourth method of cationization combines the advantages of polylysine cationization with the formation of cleavable esters to enhance blood-brain barrier transport, as well as to yield intact growth factor following transport. Polylysine may be made reactive by reaction with benzyloxylacetyl chloride followed by hydrogenation and mild esterification procedures (Hassner et al., Tet. Let. 46:4475–4478 (1978); Mihara et al., Int. J. Peptide Protein Res. 28:141–145 (1986)). Alternatively, DMF acetal derivatives capable of reacting with polylysine could be used to link polylysine to free carboxyl groups using ester linkages.

EXAMPLE 10

A further type of polypeptide modification is glycosylation: the introduction of glucose or similar residues by reductive amination using, for example, glucose and sodium cyanoborohydride ($NaCNBH_3$). Glycosylation of proteins has been shown to enhance the cellular uptake of these proteins and may prove useful for improving blood-brain barrier transport (Smith et al., Pharm. Res., in press). The procedure for glycosylation is based on the method of Schwartz et al., 1977, wherein a polypeptide such as IGF-I, IGF-II, or a functional derivative of either is combined with glucose and $NaCNBH_3$ in a molar ratio of 1:300:1600 in 200 mM phosphate buffer at pH 7 for at least 24 hr at 37° C. Unreacted entities may be removed as described in Example 6, or with lectin affinity chromatography. In previous studies using glycosylated albumin, the modified albumin was taken up by rat epididymal microvessels at a greater rate than was native albumin (Williams et al., Proc. Nat. Acad. Sci. USA 78:2393–2397 (1981)).

EXAMPLE 11

Blood-Brain Barrier Transport Model: Method of Audus et al., Ann. N.Y. Acad. Sci. 507:9–18 (1987).

Microvessel endothelial cells are isolated from the cerebral gray matter of fresh bovine brains. Brains are obtained from a local slaughter house and transported to the laboratory in ice cold minimum essential medium (MEM) with antibiotics. Under sterile conditions the large surface blood vessels and meninges are removed. The cortical gray matter is removed by aspiration, then minced into <1 mm cubes. The minced gray matter is then incubated with 0.5% dispase (BMB, Indianapolis, IN) for 3 hours at 37° C. in a shaking water bath. Following the 3 hour digestion, the mixture is concentrated by centrifugation (1000×g for 10 min.), then resuspended in 13% dextran and centrifuged for 10 min. at 5800×g. Supernatant fat, cell debris and myelin are discarded and the crude microvessel pellet is resuspended in 1 mg/ml collagenase/dispase and incubated in a shaking water bath for 5 hours at 37° C. After the 5-hour digestion, the microvessel suspension is applied to a pre-established 50% Percoll gradient and centrifuged for 10 min at $1000 \times g$. The band containing purified endothelial cells (second band from the top of the gradient) is removed and washed two times with culture medium (50% MEM/50% F-12 nutrient mix). The cells are frozen ($-80°$ C.) in medium containing 20% DMSO and 10% horse serum for later use.

After isolation, approximately $5 \times 10^5$ cells/cm$^2$ are plated on culture dishes or 5–12 μm pore size polycarbonate filters that are coated with rat collagen and fibronectin. 10–12 days after seeding the cells, cell monolayers are inspected for confluency by microscopy.

Characterization of the morphological, histochemical and biochemical properties of these cells has shown that these cells posses many of the salient features of the blood-brain barrier. These features include: tight intercellular junctions, lack of membrane fenestrations, low levels of pinocytotic activity, and the presence of gamma-glutamyl transpeptidase, alkaline phosphatase, and Factor VIII antigen activities.

The cultured cells can be used in a wide variety of experiments where a model for polarized binding or transport is required. By plating the cells in multi-well plates, receptor and non-receptor binding of both large and small molecules can be conducted. In order to conduct transendothelial cell flux measurements, the cells are grown on porous polycarbonate membrane filters (Nucleopore, Pleasanton, CA.). Large pore size filters (5–12 μm) are used to avoid the possibility of the filter's becoming the rate-limiting barrier to molecular flux. The use of these large-pore filters does not permit cell growth under the filter and allows visual inspection of the cell monolayer.

Once the cells reach confluency, they are placed in a side-by-side diffusion cell apparatus (Crown Glass, Sommerville, NJ.). For flux measurements, the donor chamber of the diffusion cell is pulsed with a test substance, then at various times following the pulse, an aliquot is removed from the receiver chamber for analysis. Radioactive or fluorescently-labelled substances permit reliable quantitation of molecular flux. Monolayer integrity is simultaneously measured by the addition of a non-transportable test substance such as sucrose or inulin and replicates of at least 4 determinations are measured in order to ensure statistical significance.

Other embodiments are within the following claims.

We claim:

1. A method of enhancing the survival of non-mitotic, cholinergic neuronal cells in a mammal, said cells being at risk of dying, said method comprising administering to said mammal an effective amount of IGF-I.

2. The method of claim 1 wherein said cells are at risk of dying in connection with amyotrophic lateral sclerosis.

3. A method of enhancing the cholinergic activity of cholinergic neurons in a mammal, said method comprising administering to said mammal an effective amount of IGF-I.

4. The method of claim 3 wherein said mammal has amyotrophic lateral sclerosis.

* * * * *

UNITED STATES PATENT AND TRADEMARK OFFICE
CERTIFICATE OF CORRECTION

Page 1 of 3

PATENT NO. : 5,093,317
DATED : March 3, 1992
INVENTOR(S) : Michael E. Lewis, et. al.

It is certified that error appears in the above-identified patent and that said Letters Patent is hereby corrected as shown below:

Add Tables I and II in column 16, line 17 before "Other embodiments are within the following claims."

Signed and Sealed this

First Day of February, 1994

Attest:

BRUCE LEHMAN

Attesting Officer

Commissioner of Patents and Trademarks

TABLE I

IGF PEPTIDE SEQUENCES

| Peptide Name | Sequence | Source | Cat.# |
|---|---|---|---|
| Human IGF-I (Somatomedin-C) | GPETL CGAEL VDALQ FVCGD RGFYF NKPTG YGSSS- -RRAPQ TGIVD ECCFR SCDLR RLEMY CAPLK PAKSA | AMGEN[1] | 14010 |
| Human IGF-I (Somatomedin-C) | GPETL CGAEL VDALQ FVCGD RGFYF NKPTG YGSSS- -RRAPQ TGIVD ECCFR SCDLR RLEMY CAPLK PAKSA | PENINSULA[2] | 9010 Lot 15578 |
| IGF-I(4-70) (Human Brain IGF) | TLCGAEL VDALQ FVCGD RGFYF NKPTG YGSSS- -RRAPQ TGIVD ECCFR SCDLR RLEMY CAPLK PAKSA | KABIGEN[3] KABIGEN[3] | Lot 88:101G Lot S:25 |
| IGF-I(24-41) | YFNKP TGYGS SSRRA PQT | PENINSULA[2] | 7308 Lot 007942 |
| | YFNKP TGYGS SSRRA PQT | BACHEM[4] | PGRO 080 Lot F297 |
| | YFNKP TGYGS SSRRA PQT | Synthetic[5] | |
| IGF-I(30-41) | GYGSS SRRAP QT | PENINSULA[2] | 7306 Lot 003251 |
| IFG-I(62-70) | APLKP AKSA | PENINSULA[2] | 7318 Lot 015726 |
| IGF-I(24-32) | YFNKP TGYG | Synthetic[5] | |
| IGF-I(24-41)-AMIDE | YFNKP TGYGS SSRRA PQT-NH$_2$ | Synthetic[6] | |
| IGF-I(33-41)-AMIDE | SSSRR APQT-NH$_2$ | Synthetic[6] | |
| 48-Acm-IGF-I(42-57)-AMIDE | GIVDE CCFRS COLRR L-NH$_2$ (Acm above second C) | Synthetic[7] | |

TABLE II

CONSERVATIVE AMINO ACID REPLACEMENTS

| For Amino Acid | Code | Replace with |
|---|---|---|
| Alanine | A | D-Ala, Gly, Aib, β-Ala, Acp, or delete |
| Arginine | R | D-Arg, Lys, D-Lys, homo-Arg, D-homo-Arg, Met, Ile, D-Met, D-Ile, Orn, D-Orn or delete |
| Asparagine | N | D-Asn, Asp, D-Asp, Glu, D-Gln, Gln, D-Gln or delete |
| Aspartic Acid | D | D-Asp, D-Asn, Asn, Glu, D-Glu, Gln, D-Gln or delete |
| Cysteine | C | D-Cys, S-Me-Cys, Met, D-Met, Thr, D-Thr, or delete |
| Glutamine | Q | D-Gln, Asn, D-Asn, Glu, D-Glu, Asp, D-Asp or delete |
| Glutamic Acid | E | D-Glu, D-Asp, Asp, Asn, D-Asn, Gln, D-Gln, or delete |
| Glycine | G | Ala, D-Ala, Pro, D-Pro, Aib, β-Ala, Acp or delete |
| Isolencine | I | D-Ile, Val, D-Val, AdaA, AdaG, Leu, D-Leu, Met, D-Met, or delete |
| Leucine | L | D-Leu, Val, D-Val, AdaA, AdaG, Leu, D-Leu, Met, D-Met or delete |
| Lysine | K | D-Lys, Arg, D-Arg, homo-Arg, D-homo-Arg, Met, D-Met, Ile, D-Ile, Orn, D-Orn or delete |
| Methionine | M | D-Met, S-Me-Cys, Ile, D-Ile, Leu, D-Leu, Val, D-Val or delete |
| Phenylalanine | F | D-Phe, Tyr, D-Thr, L-Dopa, His, D-His, Trp, D-Trp, Trans-3,4, or 5-phenylproline, Ada-A, AdaG, cis-3,4, or 5-phenylproline, Bpa, D-Bpa or delete |
| Proline | P | D-Pro, L-I-thiazolidine-4-carboxylic acid, D-or L-I-oxazolidine-4-carboxylic acid (Kauer, U.S. Patent 4,511,390), or delete |
| Serine | S | D-Ser, Thr, D-Thr, allo-Thr, Met, D-Met, Met(O)D,-Met(O) or delete |
| Threonine | T | D-Thr, Ser, D-Ser, allo-Thr, Met, D-Met, Met(O), D-Met(O), Val, D-Val or delete. |
| Tyrosine | Y | D-Tyr, Phe, D-Phe, L-Dopa, His, D-His or delete |
| Valine | V | D-Val, Leu, D-Leu, Ile, D-Ile, Met, D-Met, AdaA, AdaG or delete |